(12) United States Patent
Jones et al.

(10) Patent No.: US 10,300,157 B2
(45) Date of Patent: May 28, 2019

(54) RETAIL STORE FIXTURE AND METHOD OF STERILIZING A RETAIL STORE FIXTURE

(71) Applicant: Walmart Apollo, LLC, Bentonville, AR (US)

(72) Inventors: Matthew Allen Jones, Bentonville, AR (US); Nicholaus Adam Jones, Fayetteville, AR (US); Robert James Taylor, Rogers, AR (US)

(73) Assignee: WALMART APOLLO, LLC, Bentonville, AR (US)

( * ) Notice: Subject to any disclaimer, the term of this patent is extended or adjusted under 35 U.S.C. 154(b) by 298 days.

(21) Appl. No.: 15/381,536

(22) Filed: Dec. 16, 2016

(65) Prior Publication Data
US 2017/0174187 A1   Jun. 22, 2017

Related U.S. Application Data

(60) Provisional application No. 62/270,932, filed on Dec. 22, 2015.

(51) Int. Cl.
*A61L 2/00* (2006.01)
*B01J 19/08* (2006.01)
(Continued)

(52) U.S. Cl.
CPC .................. *A61L 2/03* (2013.01); *B62B 3/14* (2013.01); *B62B 5/06* (2013.01); *A61L 2202/14* (2013.01)

(58) Field of Classification Search
CPC .......... A61L 2/03; A61L 2202/14; B60S 1/62; B62B 3/14; B62B 5/069; H02S 10/40
(Continued)

(56) References Cited

U.S. PATENT DOCUMENTS 1,991,236 A * 2/1935 De Graaff ................ H02N 1/12
                                                         15/1.51
5,817,142 A   10/1998 Corder
(Continued)

FOREIGN PATENT DOCUMENTS

CN          205429849 U      8/2016

OTHER PUBLICATIONS

Giladi, et al., "Microbial Growth Inhibition by Alternating Electric Fields," Antimicrobial Agents and Chemotherapy, acc.asm.org, Jul. 28, 2008, American Society for Microbiology; 10 pages.
(Continued)

*Primary Examiner* — Monzer R Chorbaji
(74) *Attorney, Agent, or Firm* — Schmeiser, Olsen & Watts LLP

(57) ABSTRACT

Described is a retail store fixture that includes an electric charge circuit. The electric charge circuit generates a positive electric charge, or voltage, in response to the motion of a moveable portion of the retail store fixture. The retail store fixture can be a shopping cart or other fixture with a moveable portion. The positive electric charge is deposited on a part of the retail store fixture that it is desired to sterilize. The positive electric charge repels bacteria, sterilizing the portion of the retail store fixture that receives the positive charge. A shopping cart, for example, equipped with the electric charge circuit can be sterilized without requiring chemicals or power to be supplied to the cart. Rotation of the shopping cart wheels can be used to generate the voltage. The voltage can be used to sterilize a shopping cart handle, and/or other parts of the shopping cart.

13 Claims, 6 Drawing Sheets

(51) Int. Cl.
*A61L 2/03* (2006.01)
*B62B 3/14* (2006.01)
*B62B 5/06* (2006.01)

(58) Field of Classification Search
USPC .................................. 422/1, 22, 186.05, 292
See application file for complete search history.

(56) References Cited

U.S. PATENT DOCUMENTS

| | | | |
|---|---|---|---|
| 7,443,295 B2 | 10/2008 | Brice et al. | |
| 8,175,698 B2 | 5/2012 | Palti et al. | |
| 8,663,914 B2 | 3/2014 | Ren et al. | |
| 2006/0249320 A1* | 11/2006 | Carter | A47F 10/04 |
| | | | 180/65.51 |
| 2009/0016930 A1 | 1/2009 | Gordon | |
| 2011/0116967 A1* | 5/2011 | Roy | A61L 2/14 |
| | | | 422/22 |

OTHER PUBLICATIONS

Caubet, et al., "A Radio Frequency Electric Current Enhances Antibiotic Efficacy against Bacterial Biofilms," Antimicrobial Agents and Chemotherapy, Dec. 2004, pp. 4662-4664, Antimicrobial Agents and Chemotherapy.

* cited by examiner

RETAIL STORE FIXTURE AND METHOD OF STERILIZING A RETAIL STORE FIXTURE

CROSS REFERENCE TO RELATED APPLICATION

This invention claims priority to U.S. provisional patent application Ser. No. 62/270,932, filed Dec. 22, 2015 to Applicant Wal-Mart Stores Inc., and entitled "Retail Store Fixture and Method of Sterilizing a Retail Store Fixture", which is included entirely herein by reference.

BACKGROUND OF THE INVENTION

Technical Field

This invention relates to retail store fixtures, and, more specifically, to a retail store fixture that uses a positive electric charge to sterilize the retail store fixture.

State of the Art

Retail store fixtures such as shelves, cold storage devices, and shopping carts are used to store and deliver food stuff to consumers. It is desirable to keep retail store fixtures such as these as sterile and bacteria-free as possible. Keeping retail store fixtures bacteria-free helps prevent food from being contaminated, as well as helping to prevent from spreading bacteria from one person to another. A retail store can spend many employee hours cleaning and sanitizing retail store fixtures because there are numerous people that come into contact with the fixtures. It is desirable to have devices and methods for reducing the time and cost of sterilizing retail store fixtures.

Accordingly, what is needed is a device and method for quickly and easily sterilizing retail store fixtures at a minimum cost to the retail store.

DETAILED DESCRIPTION OF EMBODIMENTS OF THE INVENTION

Figure 1:
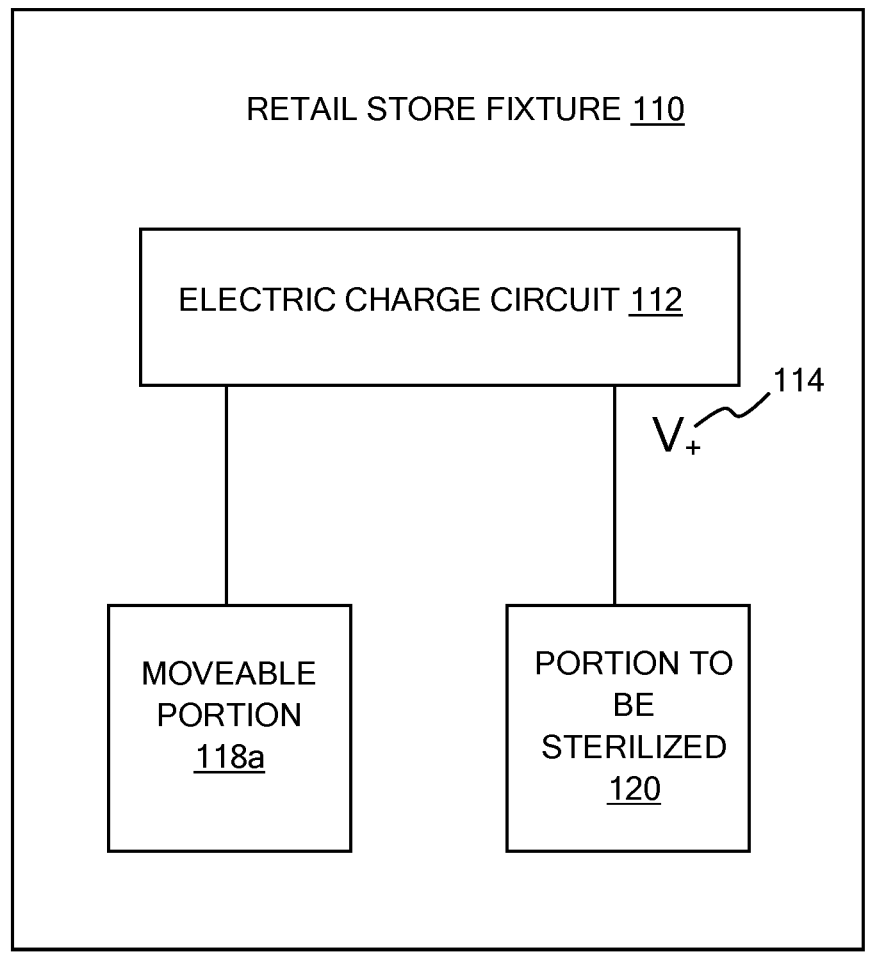
FIG. 1 shows a block diagram of an embodiment of a retail store fixture with an electric charge circuit for sterilizing the retail store fixture.

As discussed above, disclosed is an invention that relates to retail store fixtures, and, more specifically, to a retail store fixture with an electric charge circuit that generates a positive electric charge used to sterilize the retail store fixture.

Disclosed is a retail store fixture that includes an electric charge circuit. The electric charge circuit generates a positive electric charge, or voltage, in response to the motion of a moveable portion of the retail store fixture. The positive electric charge is deposited on a portion of the retail store fixture that it is desired to sterilize. The portion that receives the electric charge is sterilized in response to receiving the positive electric charge. The positive electric charge repels bacteria, sterilizing the portion receiving the electric charge. In this way, the motion of one part of the retail store fixture is used to sterilize one or more parts of the retail store fixture. This allows the retail store fixture to be sterilized without requiring chemicals to be used, or power to be supplied to the fixture. The retail store fixture can be a shopping cart, for example, or a refrigerator/freezer. Movement of the wheels of the shopping cart or the door or lid of a freezer compartment, for example, can be used by the electric charge circuit to generate a voltage. The voltage can be used to sterilize the freezer door or lid so germs are not transmitted from person to person or into the retail store fixture (shopping cart, freezer compartment, for example). In some embodiments, the retail store fixture is a bagging station carousel, where the rotation of the bagging station generates the voltage. The voltage can be used to sterilize a part of the carousel. The retail store fixture can also be an oven or a shelf with a moveable portion, or any other type of retail store fixture that it is desired to sterilize, and that has a moveable portion.

Disclosed is a retail store fixture that includes a means for generating a static charge, and a means for depositing the static charge on a portion of the retail store fixture. The retail store fixture can be a shopping cart, for example, or the door of a refrigerator or freezer, an oven, a shelf, a rotating bagging station, or a storage unit of a retail store. In some embodiments, the retail store fixture also includes a means for storing the static charge. In some embodiments, the retail store fixture also includes a means for dispersing the static charge. In some embodiments, the retail store fixture includes a means for limiting the amount of static charge. In some embodiments, the retail store fixture is a shopping cart, and the static charge is generated in response to the rotation of a wheel of the shopping cart. In some embodiments, the static charge is deposited on a handle of the shopping cart. In some embodiments, the static charge is in the form of a voltage. In some embodiments, the static charge is in the form of positively charge ions. In some embodiments, the static charge is in the form of a positive electric charge.

Figure 2:
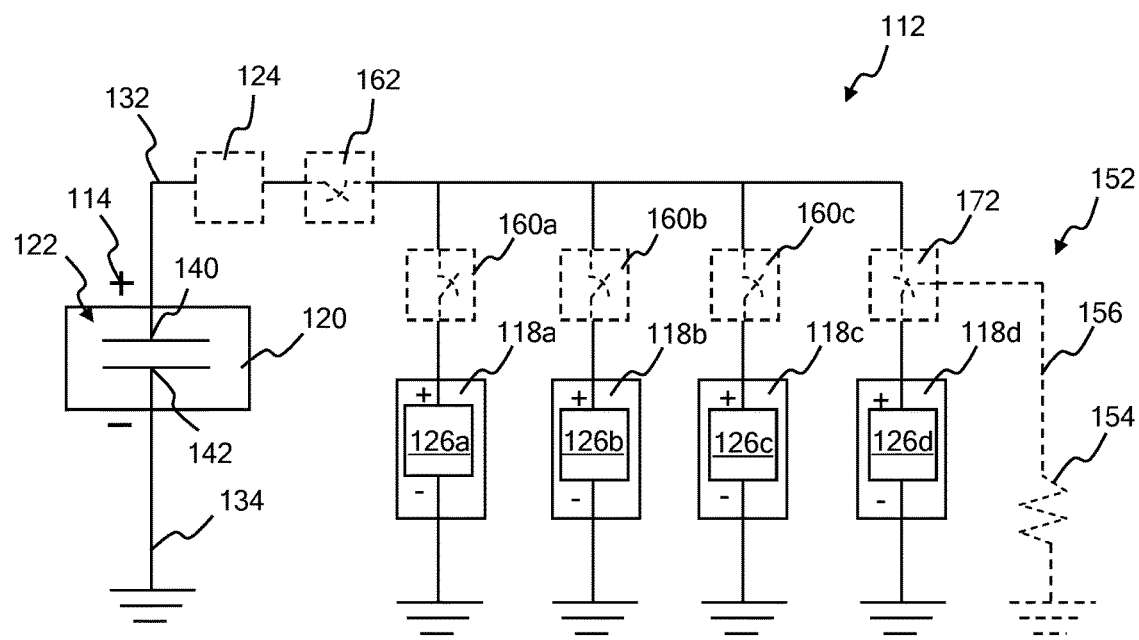
FIG. 2 shows an embodiment of an electric charge circuit for sterilizing a retail store fixture.

FIG. 1 and FIG. 2 show details of an example embodiment of a retail store fixture 110. FIG. 1 shows a simplified block diagram of retail store fixture 110 with an electric charge circuit 112. FIG. 2 shows a simplified schematic of an example of electric charge circuit 112. Referring to FIG. 1, retail store fixture 110 includes electric charge circuit 112, at least one moveable portion 118a, and at least one portion to be sterilized 120.

Moveable portion 118a can be any part or all of retail store fixture 110 that can move. In some embodiments, retail store fixture 110 is a shopping cart, and moveable portion 118a is a wheel of the shopping cart, for example (see FIG. 3 and FIG. 4). The movement can be a rotational movement, a sliding movement, the opening and closing of a door or top, or any other type of motion that can be used to generate a voltage (also referred to as an electric charge or an electrical bias). Portion to be sterilized 120 can be any part or all of retail store fixture 110 that it is desired to sterilize. "Sterilize" as used herein means to clean, and can mean to clean by repelling, disabling, or destroying bacteria. Often it is desired to sterilize portion to be sterilized 120 so that portion to be sterilized 120 does not retain and transfer bacteria from one person to another, but this is not meant to be limiting. Portion to be sterilized 120 can be sterilized for any reason.

Electric charge circuit 112 is coupled to moveable portion 118a. In some embodiments, electric charge circuit 112 is integrated into moveable portion 118a. Electric charge circuit 112 generates a voltage $V_+$ in response to a motion of moveable portion 118a. Voltage $V_+$ is labeled 114 in the drawings. Voltage 114 is also referred to as an electrical bias or an electrical charge. Electric charge circuit 112 electrically biases portion to be sterilized 120 with a positive electric charge indicated in the figures as voltage 114. Voltage 114 causes portion to be sterilized 120 to be sterilized by repelling and disabling bacteria from portion to be sterilized 120. Portion to be sterilized 120 will repel bacteria once voltage 114 is applied. Voltage 114 may, in some embodiments, disable or kill bacteria that existed on portion to be sterilized 120 before voltage 114 was applied. Voltage 114 sterilizes portion to be sterilized 120, making portion to be sterilized 120 much safer for individuals to handle. Voltage 114 will prevent portion to be sterilized 120 from transmitting or harboring bacteria.

FIG. 2 shows a simplified schematic of an example embodiment of electric charge circuit 112. In this embodiment, electric charge circuit 112 includes four voltage generators 126a, 126b, 126c, and 126d, with each voltage generator 126a, 126b, 126c, and 126d integrated into one of four moveable portions 118a, 118b, 118c, and 118d of retail store fixture 110. Retail store fixture 110 in this embodiment includes four moveable portions 118a, 118b, 118c, and 118d. Voltage generators 126a, 126b, 126c, and 126d are direct current voltage generators in this embodiment, but this is not meant to be limiting. Voltage generators 126a, 126b, 126c, and 126d are means to generate a voltage, an electric charge, or a static charge. Each voltage generator 126a, 126b, 126c, and 126d can be any type of voltage generator. Electric charge circuit 112 can include many different types of positive charge generators, static charge generators, charged ion generator, or voltage generators that are used together with, or instead of, voltage generators 126a, 126b, 126c, and 126d as shown in FIG. 2. In some embodiments, electric charge circuit 112 includes a Van de Graaf generator instead of voltage generators 126a, 126b, 126c, and 126d. Any type of charge generator, ion generator, voltage generator, or other device that generates a voltage or an electric charge can be used in place of, or in addition to, voltage generators 126a, 126b, 126c, and 126d. Electric charge circuit 112 includes at least one voltage generator. In some embodiments, electric charge circuit 112 includes one voltage generator. In some embodiments, electric charge circuit 112 includes more than one voltage generator.

Electric charge circuit 112 includes at least one voltage generator and least one capacitor. Electric charge circuit 112 as shown in FIG. 2 includes four voltage generators 126a, 126b, 126c, and 126d and one capacitor 122. Voltage generators 126a, 126b, 126c, and 126d are each contained within a corresponding moveable portion 118a, 118b, 118c, and 118d as shown in FIG. 2. Electric charge circuit 112, in general, includes one or more voltage generator, each associated with (coupled to, contained within, integrated with, etc.) a moveable portion. The number of voltage generators and moveable portions varies with different embodiments and different retail store fixtures 110, and can be any positive integer. Each voltage generator 126a, 126b, 126c, and 126d generates a voltage in response to movement of a corresponding moveable portion 118a, 118b, 118c, and 118d. Voltage 114, the sum of the voltages generated by voltage generators 126a, 126b, 126c, and 126d, is delivered on a conductor 132 to portion to be sterilized 120. Each voltage generator 126a, 126b, 126c, and 126d is a means for generating a voltage or an electric charge or a static charge. In this embodiment, voltage 114 is delivered to capacitor 122 that is a part of portion to be sterilized 120. Capacitor 122 has a positive terminal 140 electrically connected to conductor 132, and a negative terminal 142 electrically coupled to a current return path 134, as shown in FIG. 2. Capacitor 122 in this embodiment is a means to store voltage 114. Capacitor 122 is a means to store a voltage, a means to store an electric charge, and a means to store a static charge. In some embodiments, retail store fixture 110 includes more than one portion to be sterilized 120. In some embodiments, retail store fixture 110 includes more than one capacitor 122.

In some embodiments, electric charge circuit 112 includes a voltage regulator 124 (shown in dotted lines as optional in FIG. 2). Voltage generators 126a, 126b, 126c, and 126d are electrically coupled to capacitor 122 through voltage regulator 124 when voltage generator 124 is used. Voltage regulator 124 is a means to regulate voltage 114. Voltage regulator 124 is used to regulate voltage 114 sent to portion to be sterilized 120. Voltage regulator 124 can be used to ensure voltage 114 does not get too large, for example, that it becomes dangerous for individuals to touch portion to be sterilized 120.

In some embodiments, electric charge circuit 112 includes one or more than one switch. For example, electric circuit 112 can include any one or more of optional switches 160a, 160b, 160c, 162 or 172, shown in dotted lines in FIG. 2 to indicate that they are optional. Each of one or more switch 160a, 160b, 160c, 162, or 172 disconnects portions of electric charge circuit 112 from each other, as shown in FIG. 2 and described below.

In the embodiment shown in FIG. 2, optional switch 162 electrically disconnects all voltage generators 126a, 126b, 126c, and 126d from portion to be sterilized 120. In this embodiment, switch 162 electrically disconnects voltage generators 126a, 126b, 126c, and 126d from capacitor 122 of portion to be sterilized 120. Example reasons to electrically disconnect all voltage generators 126a, 126b, 126c, and 126d from portion to be sterilized 120 include, but are not limited to, one or more of voltage generators 126a, 126b, 126c or 126d is generating too much voltage; one or more of voltage generators 126a, 126b, 126c, or 126d is not generating any voltage; and it is no longer desired to sterilize portion to be sterilized 120.

In the embodiment shown in FIG. 2, switches 160a, 160b, and 160c each disconnect an individual voltage generator 126a, 126b, or 126c from portion to be sterilized 120 when they are used in electric charge circuit 112. Switch 160a disconnects voltage generator 126a from portion to be sterilized 120, without affecting the connection between voltage generator 126b, 126c, and 126d and portion to be sterilized 120. Example reasons to electrically disconnect voltage generator 126a from portion to be sterilized 120 include, but are not limited to, voltage generator 126a is generating too much voltage; voltage generator 126a is not generating any voltage; and it is no longer desired to sterilize portion to be sterilized 120. Switch 160b disconnects voltage generator 126b from portion to be sterilized 120, without affecting the connection between voltage generator 126a, 126c, and 126d and portion to be sterilized 120. Example reasons to electrically disconnect voltage generator 126b from portion to be sterilized 120 include, but are not limited to, voltage generator 126b is generating too much voltage; voltage generator 126b is not generating any voltage; and it is no longer desired to sterilize portion to be sterilized 120. Switch 160c disconnects voltage generator 126c from portion to be sterilized 120, without affecting the connection between voltage generator 126*a*, 126*b*, and 126*d* and portion to be sterilized 120. Example reasons to electrically disconnect voltage generator 126*c* from portion to be sterilized 120 include, but are not limited to, voltage generator 126*c* is generating too much voltage; voltage generator 126*c* is not generating any voltage; and it is no longer desired to sterilize portion to be sterilized 120.

In the embodiment shown in FIG. 2, switch 172 disconnects voltage generator 126*d* from conductor 132, capacitor 122, and portion to be sterilized 120, and connects voltage generator 126*d* to an optional charge dispersal circuit 152. In some embodiments, electric charge circuit 112 includes charge dispersal circuit 152, as shown in FIG. 2 in dotted lines to indicate it is optional. Charge dispersal circuit 152 is a means for dispersing voltage 114. Charge dispersal circuit 152 can be a means for dispersing an electric charge or a static charge. Charge dispersal circuit 152 is a means to disperse, or drain, the voltage generated by voltage generator 126*d*, where disperse means to route the voltage to a load other than portion to be sterilized 120. In the embodiment shown, switch 172 in a first position sends the voltage generated by voltage generator 126*d* to portion to be sterilized 120. In a second position of switch 172, switch 172 sends the voltage generated by voltage generator 126*d* to charge dispersal circuit 152 instead of to portion to be sterilized 120. When switch 172 sends the voltage generated by voltage generator 126*d* to charge dispersal circuit 152, the voltage is sent to load 154, which in this embodiment is a resistor. In this way, switch 172 in a second position is used to direct the voltage generated by voltage generator 126*d* to charge dispersal circuit 152 instead of to portion to be sterilized 120.

Electric charge circuit 112 uses one or more of voltage generators 126*a*, 126*b*, a26*c*, or 126*d*, or other charge generation devices, to generate a voltage 114. Voltage 114 is generated in response to movement of moveable portions 118*a*, 118*b*, 118*c*, and 118*d*. Electric charge circuit 112 does not need external power or batteries to generate voltage 114, and so electric charge circuit is power efficient. Voltage 114 is sent to portion to be sterilized 120. Voltage 114 sterilizes portion to be sterilized 120 by repelling bacteria and, in some embodiments, disabling or killing bacteria. Voltage 114 keeps portion to be sterilized 120 clean so that individuals touching portion to be sterilized 120 do not get contaminated with bacteria by touching portion to be sterilized 120. And voltage 114 repels bacteria which could be transferred from an individual touching portion to be sterilized 120.

Figure 3:
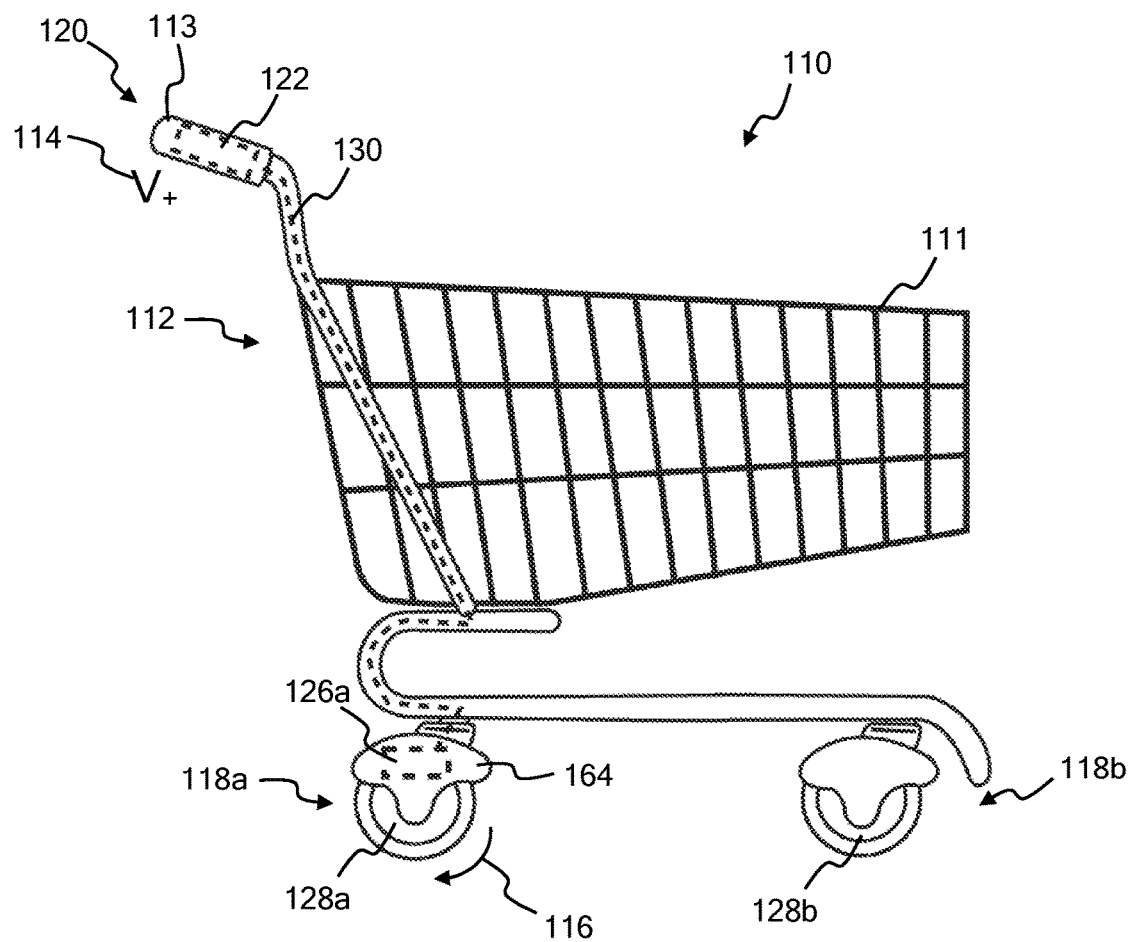
FIG. 3 shows a simplified drawing of the retail store fixture of FIG. 1 with an electric charge circuit for sterilizing the retail store fixture.
Figure 4:
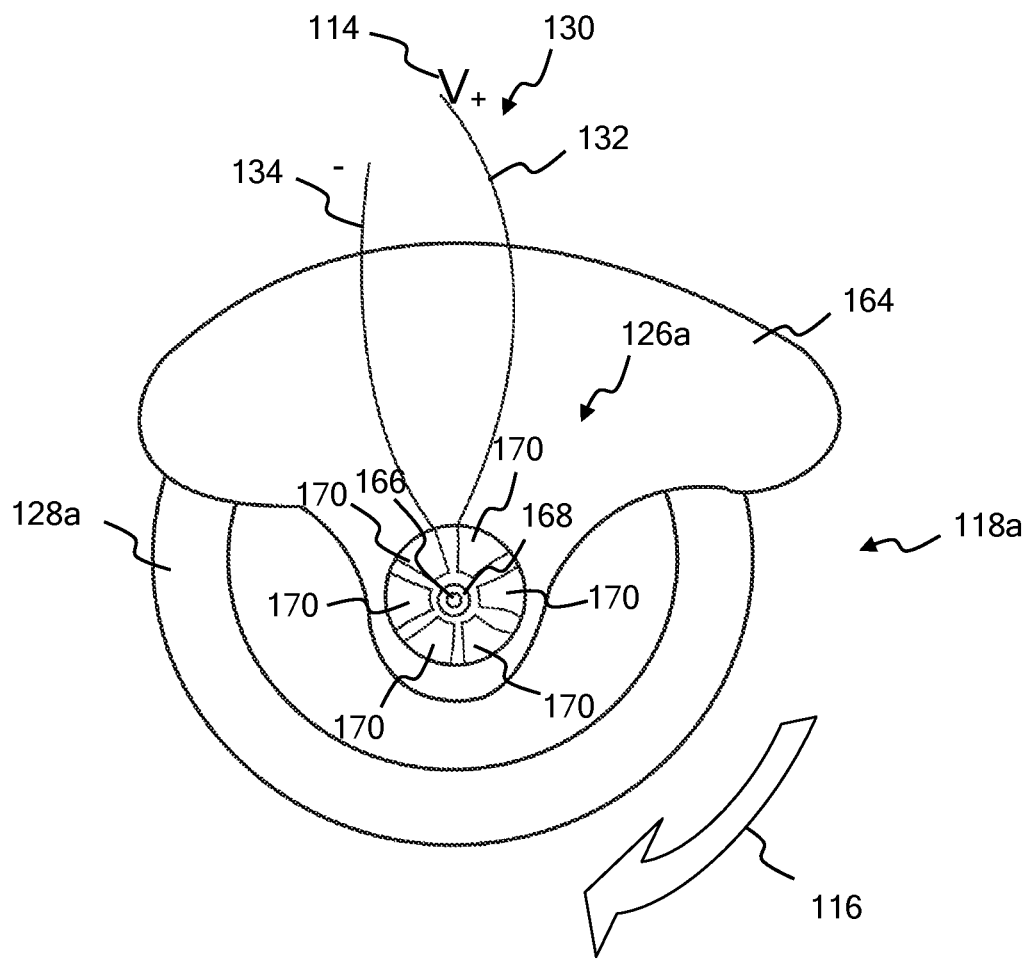
FIG. 4 shows a wheel of the retail store fixture of FIG. 3 with a voltage generator of an electric charge circuit in the wheel.
Figure 5:
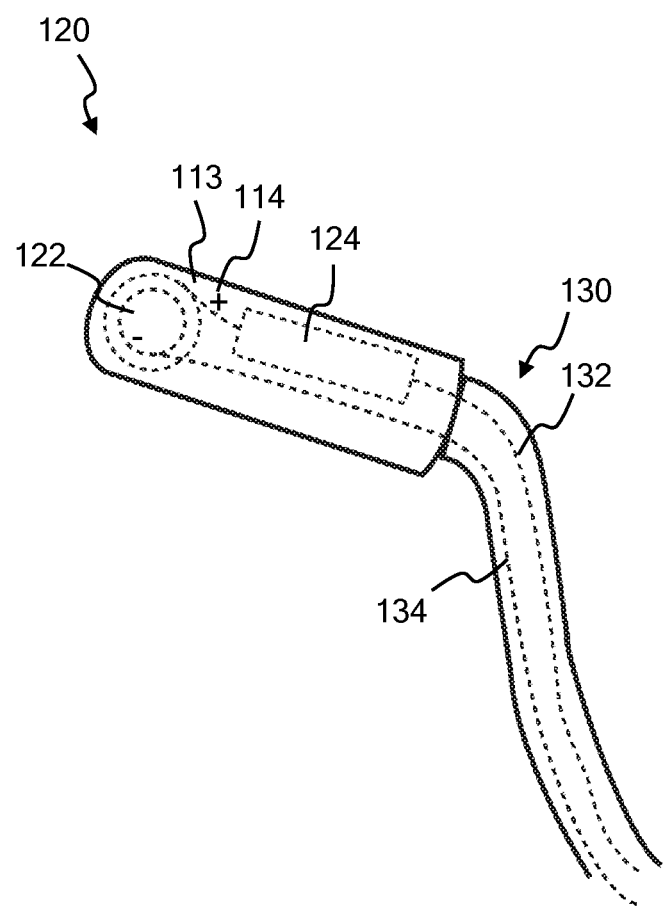
FIG. 5 shows a handle of the retail store fixture of FIG. 3 with a capacitor of an electric charge circuit in the handle.

FIG. 3, FIG. 4, and FIG. 5 show a simplified drawing of retail store fixture 110, with retail store fixture 110 including a shopping cart body 111. FIG. 3 shows a side view of shopping cart body 111 of retail store fixture 110. FIG. 4 shows a close-up side view of moveable portion 118*a*, which in this embodiment includes a wheel 128*a* of shopping cart body 111. FIG. 5 shows a close-up side view of portion to be sterilized 120, which in this embodiment includes a handle 113 of shopping cart body 111 and capacitor 122.

Retail store fixture 110 includes shopping cart body 111, portion to be sterilized 120, moveable portion 118*a*, and electric charge circuit 112. In this embodiment, portion to be sterilized 120 includes handle 113 and capacitor 122. Moveably portion 118*a* includes wheel 128*a*. Shopping cart body 111 in this embodiment includes moveably portion 118*b*, which includes wheel 128*b*. Shopping cart body 111 in this embodiment also includes moveably portion 118*c* and 118*d*, which include the other two wheels of shopping cart body 111, not shown in the figures for simplicity.

Shopping cart body 111 includes electric charge circuit 112. Electric charge circuit 112 electrically biases portion to be sterilized 120 of shopping cart body 111 with a positive electric charge, which in this embodiment is voltage 114. Portion to be sterilized 120 in this embodiment includes shopping cart handle 113 and capacitor 122 (FIG. 3 and FIG. 5). In some embodiments, portion to be sterilized 120 is a different portion of shopping cart body 111, such as a child seat, a cage portion, or the whole shopping cart body 111, for example. Portion to be sterilized 120 can be any portion of shopping cart body 111 that it is desired to sterilize.

Electric charge circuit 112 electrically biases portion to be sterilized 120, using voltage 114 in this embodiment, in response to a motion of moveable portion 118*a*. In the embodiment shown in FIG. 3 and FIG. 4, portion to be sterilized 120 is handle 113, and moveable portion 118*a* includes wheel 128*a*. Wheel 128*a* moves in rotation 116. Thus, in the embodiment shown in FIG. 3 and FIG. 4, electric charge circuit 112 electrically biases shopping cart handle 113 and capacitor 122 in response to a rotation 116 of wheel 128*a* (FIG. 3 and FIG. 4).

Electric charge circuit 112 is distributed on shopping cart body 111 as shown in FIG. 3, FIG. 4, and FIG. 5. Handle 113 includes capacitor 122 and voltage regulator 124, as shown in FIG. 2, FIG. 3 and FIG. 5. In this embodiment, capacitor 122 is embedded in handle 113 so that voltage 114 stored on capacitor 122 results in handle 113 being electrically biased with a positive electric charge. Electric charge circuit 112 electrically biases handle 113 with voltage 114, where in this embodiment, voltage 114 is a positive electric charge. In this embodiment, voltage regulator 124 is also embedded in handle 113.

Voltage generator 126*a* is integrated into wheel 128*a*, as shown in FIG. 2, FIG. 3 and FIG. 4. Pair of conducting wires 130, which includes positive conductor 132 and current return path 134 (FIG. 2 and FIG. 5), extend from handle 113 to wheel 128*a* as shown in FIG. 3, FIG. 4, and FIG. 5. Pair of conducting wires 130, which includes positive conductor 132 and current return path 134, are a means for depositing voltage (positive charge) 114 on capacitor 122 of handle 113. Motion 116 of wheel 128*a* causes voltage generator 126*a* to generate positive charge 114. Positive charge 114 is conducted to capacitor 122 of handle 113 of shopping cart body 111, sterilizing capacitor 120 and handle 113.

FIG. 4 shows an enlarged drawing of wheel 128*a* and voltage generator 126*a* of shopping cart body 111. Voltage generator 126*a* is coupled to wheel 128*a* of shopping cart body 111. Voltage generator 126*a* in this embodiment is integrated into wheel cover 164 of wheel 128*a*. Voltage generator 126*a* in this embodiment is a direct current voltage generator, but this is not meant to be limiting. Voltage generator 126*a*, in the embodiment shown in FIG. 4, includes a brush 166, a lap winding core 168, and a plurality of field poles, or magnets, 170. Rotation 116 of wheel 128*a* causes field poles 170 to rotate with respect to lap winding core 168, generating a current in lap winding core 168, which current generates a positive electric charge, or voltage, 114. In this way, direct current voltage generator 126*a* generates a voltage 114 in response to rotation 116 of wheel 128*a*.

It is to be understood that voltage generator 126*a* can be any type of device that generates a voltage or electric charge in response to a movement of moveable portion 118*a*. In some embodiments, voltage generator 126*a* is a Van de Graaf generator. In some embodiments, voltage generator 126*a* is a DC voltage generator as shown in FIG. 4. In some embodiments, voltage generator 126*a* is a different device that generates an electric charge in response to movement of moveable portion 118a. Voltage generator 126a is integrated into wheel 128a of shopping cart body 111 in this embodiment, but it is to be understood that voltage generator 126a can be integrated into any moveable portion of retail store fixture 110, such as a hinge of a freezer door, for example, a building door, a lid of a freezer or storage or display fixture, a rotating bagging carousel, or any other moveable portion of retail store fixture 110.

In some embodiments, wheel 128a includes a switch 160a and/or 172 as shown in FIG. 2 in dotted lines and described in the accompanying text. In some embodiments, wheel 128 includes switch 162 of electric charge circuit 112, where switch 162 connects and disconnects voltage generator 126a from capacitor 122. In some embodiments, wheel 128a includes other switches or electrical components that are a part of electric charge circuit 112. In some embodiments, wheel 128a includes a charge dispersal circuit 152, as shown in FIG. 2 in dotted lines and described in the accompanying text. In some embodiments, charge dispersal circuit 152 is coupled to wheel 128a. Charge dispersal circuit 152 can be used to disperse voltage 114 when shopping cart body 111 is not moving, when no user is in contact with shopping cart 111, or when voltage 114 gets to a predetermined level, for example. In some embodiments, charge dispersal circuit 152 drains voltage 114 in response to a lack of motion of wheel 128a. In some embodiments, wheel 128a and electric charge circuit 112 includes other elements which can switch voltage 114 on and off based on specific triggers or timers. In some embodiments, electric circuit 112 can send voltage 114 to charge dispersal circuit 152 if there is no movement of wheel 128 for a predetermined amount of time.

Pair of conductors 130, which includes positive conductor 132 and current return path (ground conductor) 134, conducts voltage 114 to shopping cart handle 113, as can be seen in FIG. 3, FIG. 4, and FIG. 5. Handle 113 includes capacitor 122, as shown in FIG. 2 and FIG. 5. Capacitor 122 stores voltage 114 on handle 113. Voltage 114 being stored on handle 113 sterilizes handle 113, so that handle 113 has minimal bacteria, keeping handle 113 clean for individuals who are operating shopping cart body 111. In this embodiment, handle 113 also includes voltage regulator 124 (FIG. 2 and FIG. 5), which regulates voltage 114 to ensure voltage 114 does not reach levels which would be dangerous or annoying for users of shopping cart body 111. Voltage regulator 124 is a means for limiting voltage 114 so that voltage 114 does not increase to dangerous levels. Voltage regulator 124 is a means for limiting the amount of static charge on handle 113. Voltage regulator 124 is also a means for limiting the amount of electrical bias of handle 113. In some embodiments, handle 113 includes a plurality of capacitors in series that replace capacitor 122. Using a plurality of capacitors in series to replace one capacitor 122 can help to regulate the voltage level on the plurality of capacitors, ensuring that voltage 114 does not get to an annoying or dangerous level. In some embodiments, handle 113 includes optional switch 162 for disconnecting voltage generator 126a from capacitor 122.

It has been explained how the use of an electric charge circuit can be used as part of a retail store fixture to generate a voltage for sterilizing a portion of the retail store fixture. The electric charge circuit uses motion of a moveable part of the retail store fixture to generate the voltage. The electric charge circuit used as part of the retail store fixture provides a simple, low energy usage device for sterilizing retail store fixtures. The generated voltage will repel and disable bacteria on the retail store fixture, helping to sanitize the retail store fixture, and eliminate bacteria transferring from one user to another via the retail store fixture.

Figure 6:
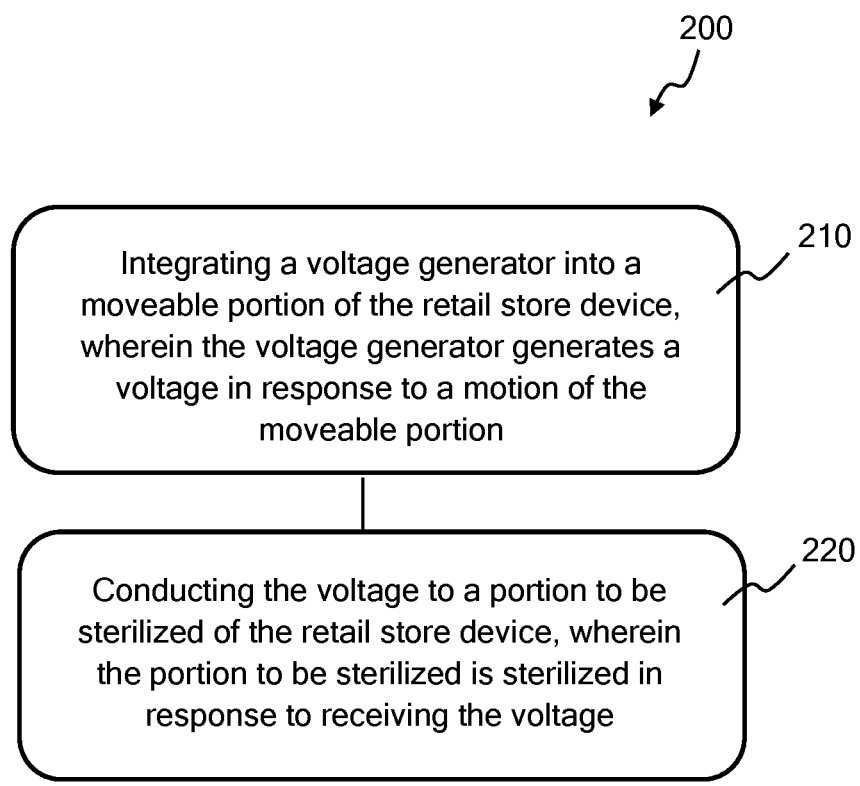
FIG. 6 illustrates a method of sterilizing a retail store fixture.

FIG. 6 illustrates a method 200 of sterilizing a retail store device. The retail store device can be a shopping cart, a refrigerator/freezer, or any other retail store fixture that has a moveable portion. Method 200 includes an act 210 of integrating a voltage generator into a moveable portion of the retail store device, where the voltage generator generates a voltage in response to a motion of the moveable portion. The moveable portion can be a wheel of a shopping cart. The moveable portion can be a door of a refrigerator/freezer. The moveable portion can be a moving carousel of a bagging station.

Method 200 also includes an act 220 of conducting the voltage to a portion to be sterilized of the retail store device, where the portion to be sterilized of the retail store device is sterilized in response to receiving the voltage. In some embodiments, the portion to be sterilized is a handle of a shopping cart. In some embodiments, the portion to be sterilized is a door handle of a refrigerator/freezer.

Method 200 can include many other acts. In some embodiments, method 200 includes an act of storing the voltage generated by the voltage generator. In some embodiments, method 200 includes an act of storing the voltage generated by the voltage generator in a capacitor. In some embodiments, method 200 includes an act of regulating the voltage generated by the voltage generator. In some embodiments, method 200 includes an act of draining the voltage in response to lack of motion of the moveable portion. In some embodiments, method 200 includes an act of dissipating the voltage through a resistor in response to lack of motion of the moveable portion.

Disclosed is a method of sterilizing a shopping cart. The method of sterilizing a shopping cart includes an act of integrating a voltage generator into a wheel of the shopping cart, where the voltage generator generates a voltage in response to a rotation of the wheel. The method of sterilizing a shopping cart includes an act of conducting the voltage to a handle of the shopping cart, where the handle is sterilized in response to receiving the voltage. The method of sterilizing a shopping cart can include many other acts. In some embodiments, the method of sterilizing a shopping cart includes an act of regulating the voltage generated by the voltage generator. In some embodiments, the method of sterilizing a shopping cart includes an act of draining the voltage in response to lack of rotation of the wheel. In some embodiments, conducting the voltage to the handle of the shopping cart includes conducting the voltage to a capacitor in the handle of the shopping cart. In some embodiments, the method of sterilizing a shopping cart includes an act of electrically disconnecting the voltage generator from the capacitor in response to lack of movement of the wheel for a predetermined amount of time.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above.

The invention claimed is:

1. A shopping cart comprising a handle, a wheel and an electric charge circuit, wherein the electric charge circuit electrically biases the handle of the shopping cart with a positive electric charge, wherein the electric charge circuit comprises:
- a charge generator in the wheel of the shopping cart;
- a capacitor embedded in the handle;
- a voltage regulator embedded in the handle; and
- a switch, wherein the switch connects and disconnects the charge generator from the capacitor, wherein the charge generator is electrically coupled to the capacitor through the voltage regulator, and wherein the charge generator is electrically disconnected in response to lack of rotation of the wheel.

2. The shopping cart of claim 1, wherein the charge generator is a voltage generator.

3. The shopping cart of claim 2, wherein the electric charge circuit electrically biases the handle in response to a rotation of the wheel of the shopping cart.

4. The shopping cart of claim 3, wherein the voltage generator is a direct current voltage generator, and wherein the direct current voltage generator generates a voltage in response to a rotation of the wheel of the shopping cart.

5. The shopping cart of claim 4, wherein the direct current voltage generator is coupled to the wheel of the shopping cart.

6. The shopping cart of claim 5, wherein the electric charge circuit further comprises a charge dispersal circuit, and wherein the charge dispersal circuit is coupled to the wheel of the shopping cart.

7. The shopping cart of claim 1, wherein the switch is in the handle.

8. The shopping cart of claim 1, wherein the charge generator is a Van de Graaff generator.

9. The shopping cart of claim 1, wherein the voltage regulator limits the electrical bias of the handle.

10. The shopping cart of claim 1, wherein the switch is in the wheel.

11. A method of sterilizing a handle of a shopping cart, the method comprising:
- integrating a voltage generator into a wheel of the shopping cart, wherein the voltage generator generates a voltage in response to a rotation of the wheel;
- conducting the voltage to a capacitor in the handle of the shopping cart, wherein the handle is sterilized in response to receiving the voltage;
- regulating the voltage in the handle generated by the voltage generator with a voltage regulator in the handle of the shopping cart;
- draining the voltage in response to lack of the rotation of the wheel; and
- electrically disconnecting the voltage generator from the capacitor with a switch in response to the lack of the rotation of the wheel for a predetermined amount of time.

12. The method of claim 11, wherein the switch is in the handle.

13. The method of claim 11, wherein the switch is in the wheel.

* * * * *